United States Patent [19]

Jacobson et al.

[11] Patent Number: 5,583,124
[45] Date of Patent: Dec. 10, 1996

[54] BISPHOSPHORYL HYDRAZINES AND THEIR USE AS PESTICIDES

[75] Inventors: Richard M. Jacobson, Chalfont; Luong T. Nguyen, Lansdale, both of Pa.

[73] Assignee: Rohm and Haas Company, Philadelphia, Pa.

[21] Appl. No.: 471,955

[22] Filed: Jun. 6, 1995

Related U.S. Application Data

[62] Division of Ser. No. 248,942, May 25, 1994, Pat. No. 5,461,038, which is a continuation of Ser. No. 866,084, Apr. 3, 1992, abandoned, which is a continuation of Ser. No. 463,746, Jan. 12, 1990, abandoned.

[51] Int. Cl.$^6$ .......................... A01N 57/30; A01N 57/28; C07F 9/24
[52] U.S. Cl. ........................ 514/102; 514/107; 558/154
[58] Field of Search ...................... 514/102, 107; 558/154

[56] References Cited

U.S. PATENT DOCUMENTS

| | | |
|---|---|---|
| 2,945,055 | 7/1960 | Tolkmith . |
| 2,968,668 | 1/1961 | Tolkmith . |
| 3,047,624 | 7/1962 | Tolkmith . |
| 3,954,439 | 5/1976 | Papamichael et al. . |
| 4,203,979 | 5/1980 | Brown . |

FOREIGN PATENT DOCUMENTS 1433882  4/1976  United Kingdom .

OTHER PUBLICATIONS

"Hydrazides of Methylphosphonic and Methylthiophosphonic Esters", Englin, M.S. et al., CA69, pp. 4882, 52212 (1968).

"Synthesis of Carbon-Phosphorous Bonds", Robert Engel, p. 172, CRC Press (1988).

*Primary Examiner*—Johann Richter
*Assistant Examiner*—Michael G. Ambrose
*Attorney, Agent, or Firm*—Thomas D. Rogerson

[57] ABSTRACT

This invention relates to bisphosphoryl hydrazine compounds and to compositions thereof which are useful as pesticides. The compounds of this invention are effective against soil insects, especially the corn rootworm.

3 Claims, No Drawings

BISPHOSPHORYL HYDRAZINES AND THEIR USE AS PESTICIDES

This is a divisional of application Ser. No. 08/248,942, filed May 25, 1994, now U.S. Pat. No. 5,461,038 which is a continuation of U.S. Ser. No. 07/866,084, filed Apr. 3, 1992, now abandoned; which is a continuation of U.S. Ser. No. 07/463,746, filed Jan. 12, 1990, now abandoned.

BACKGROUND OF THE INVENTION

1. Field of the Invention.

This invention relates to novel bisphosphoryl derivatives of hydrazine, and to compositions thereof which are useful in controlling agricultural pests such as insects, especially the corn rootworm.

Of the insects and other pests which attack the corn plant, the corn rootworm is particularly difficult to control. Corn rootworms are the larvae of beetles of the genus Diabrotica which cause damage to corn plants, especially in fields where one corn crop follows another in successive seasons. The adult beetles lay eggs in the soil of a maturing crop where the eggs lie dormant until Spring; the hatching larvae feed on the roots of young corn plants reducing yield or causing the plants to topple over under influence of climatic conditions. The fallen stalks cannot be harvested by mechanical means, and significant loss of yield results. Control of soil insects such as the corn rootworm is difficult because most pesticides are quickly inactivated by soil bacteria and fail to control the insect population throughout the growing season.

We have found that bisphosphoryl hydrazine compounds are active in the soil for a sufficient period of time to control the corn rootworm as well as other insect pests such as turf grubs and have low toxicity to mammals.

2. Description of the Prior Art.

Tolkmith (U.S. Pat. No. 2,968,688) describes compounds of the general formula:

$$\begin{array}{c} R \diagdown \underset{\|}{S} \qquad \underset{\|}{S} \diagup R \\ \phantom{R}\diagup P-NHNH-P\diagdown \\ R' \qquad\qquad\qquad R' \end{array}$$

wherein R and R' are radicals containing up to four carbon atoms which are lower alkoxy, mono-lower alkylamino radicals or di-lower alkylamino radicals wherein each of the alkyl groups contains up to four carbon atoms. R and R' may be the same or different radicals. These compounds are active as herbicides and systemic insecticides, especially for the mexican bean beetle.

Tolkmith (U.S. Pat. No. 2,945,055) reports a general compound structure of the type:

$$\begin{array}{c} R \diagdown \underset{\|}{S} \qquad \underset{\|}{S} \diagup R \\ \phantom{R}\diagup P-NHNH-P\diagdown \\ R' \qquad\qquad\qquad R' \end{array}$$

wherein R and R' have the same definition as in U.S. Pat. No. 2,968,688. The U.S. Pat. No. '055 structures are unsymmetrical while the U.S. Pat. No. '688 compounds are symmetrical. These compounds are reported to be fungicides and insecticides against the southern armyworm. There is no reported activity against the corn rootworm.

Englin, et al., *CA* 69 p. 4882, 52212 (1968) describe the preparation of compounds represented by the following structure:

$$\begin{array}{c} CH_3 \diagdown \underset{\|}{O} \qquad \underset{\|}{O} \diagup CH_3 \\ \phantom{CH_3}\diagup P-NHNH-P\diagdown \\ RO \qquad\qquad\qquad OR \end{array}$$

wherein R is isobutyl. These products were prepared for evaluation as biocides.

SUMMARY OF THE INVENTION

This invention relates to bisphosphoryl hydrazine compounds and compositions thereof which are effective as pesticides when applied to the soil or foliage of a plant. These compounds and compositions provide a method for controlling the corn rootworm and other pests.

DETAILED DESCRIPTION OF THE INVENTION

The present invention comprises a compound represented by the general formula:

$$\begin{array}{c} R^1 \diagdown \qquad\qquad\qquad R^3 \diagup \\ \phantom{R^1}O\diagdown \underset{\|}{S} \qquad \underset{\|}{Y} \diagup X^3 \\ \phantom{RRRR}P-NHNH-P \\ \phantom{RR}\diagup X^2 \qquad\qquad X^4 \diagdown \\ R^2 \diagup \qquad\qquad\qquad\qquad R^4 \end{array} \qquad (I)$$

wherein $R^1$ is selected from the group consisting of $(C_1-C_4)$ alkyl which has no branching on the carbon adjacent to the oxygen, $(C_3-C_8)$ alkenyl or $(C_3-C_8)$ alkynyl wherein these substituents may be substituted with one or more halogen, cyano, $(C_1-C_6)$ alkoxy, halo $(C_1-C_6)$ alkoxy, keto, carbo $(C_1-C_6)$ alkoxy, or $(C_1-C_6)$ acyl groups;

Y is oxygen or sulfur; and $X^2$, $X^3$ and $X^4$ are independently a phosphorus to carbon bond, sulfur, oxygen, NH or NR; and R, $R^2$, $R^3$, and $R^4$ are independently selected from the group consisting of $(C_1-C_{10})$ alkyl, $(C_3-C_{10})$ alkenyl, $(C_3-C_{10})$alkynyl, $(C_3-C_{10})$ cycloalkyl, $(C_3-C_{10})$ cycloalkyl $(C_1-C_6)$ alkyl, $(C_1-C_4)$ phenalkyl wherein these substituents may be substituted by one or more $(C_1-C_6)$ alkyl, halo $(C_1-C_6)$ alkyl, halogen, cyano, $(C_1-C_6)$ alkoxy, halo $(C_1-C_6)$ alkoxy, keto, carbo $(C_1-C_6)$ alkoxy or $(C_1-C_6)$ acyl groups; and $R^3$ and $R^4$ may be joined to form a heterocyclic ring with up to seven atoms; and $X^4$ and $R^4$ may in combination by a pyrrolidine or piperidine ring; and with the proviso that only one of $R^2$, $R^3$ and $R^4$ may be a cycloalkyl group; and with the further proviso that if Y is sulfur, $R^1$ and $R^2$ are identical, $X^2$ is oxygen, $X^3$ and $X^4$ are identical and $R^3$ and $R^4$ are identical; or $X^2$ and $X^4$ are identical, $R^2$ and $R^4$ are identical, $X^3$ is oxygen and $R^1$ and $R^3$ are identical; at least one of $R^1$, $R^2$, $R^3$ or $R^4$ must be a group other than $(C_1-C_4)$ alkyl.

In a preferred embodiment, this invention comprises a compound according to formula (I) where $R^1$ is selected from $(C_1-C_4)$ alkyl which has no branching at the carbon adjacent to the oxygen atom and wherein the alkyl group may be substituted with from one to six halogen atoms; Y is sulfur or oxygen; $X^2$ and $X^3$ are oxygen; $X^4$ is oxygen or sulfur; $R^2$, $R^3$ and $R^4$ are independently selected from optionally substituted $(C_1-C_6)$ alkyl or optionally substituted ($C_3$–$C_6$) alkenyl wherein the substituent may be from one to six halogen atoms.

In a more preferred embodiment this invention comprises a compound according to formula (I) wherein: $R^1$ is ($C_1$–$C_4$) alkyl wherein said alkyl is not branched at the carbon adjacent to the oxygen atom; $R^2$ is substituted or unsubstituted ($C^1$–$C^5$) alkyl wherein the substituent may be from three to six fluorine atoms; $R^3$ is ($C_1$–$C_5$) alkyl; $R^4$ is substituted or unsubstituted ($C_1$–$C_5$) alkyl wherein the substituent may be from three to six fluorine atoms; $X^2$, $X^3$ and $X^4$ are oxygen; and Y is sulfur.

In the most preferred embodiment, this invention comprises a compound according to formula (I) wherein:

$R^1$ is ($C_1$–$C_3$) unbranched alkyl; $R^2$ is ($C_1$–$C_5$) alkyl; $R^3$ is ($C_2$–$C_5$) alkyl; $R^4$ is ($C_4$–$C_5$) alkyl; $X^2$, $X^3$ and $X^4$ are oxygen; and Y is sulfur; branched alkyl groups are further preferred in the $R^4$ position.

In another aspect, this invention comprises a pesticidal or insecticidal composition comprising a pesticidally or insecticidally effective amount of the compound of formula (I) as defined above and an agronomically acceptable inert carrier.

In yet another aspect, this invention comprises a method of controlling insects especially soil insects such as the corn rootworm which comprises applying to said insects or corn rootworms or to the soil or to loci of plants to be freed from infestation, a pesticidally or insecticidally effective amount of a compound having the formula (I)

wherein $R^1$ is selected from the group consisting of ($C_1$–$C_4$) alkyl which has no branching on the carbon adjacent to the oxygen atom, ($C_3$–$C_8$) alkenyl or ($C_3$–$C_8$) alkynyl wherein these substituents may be substituted with one or more halogen, cyano, ($C_1$–$C_6$) alkoxy, halo($C_1$–$C_6$) alkoxy, keto, carbo ($C_1$–$C_6$) alkoxy or ($C_1$–$C_6$) acyl groups;

Y is oxygen or sulfur;

$X^2$, $X^3$ and $X^4$ are independently a phosphorus to carbon bond, sulfur, oxygen, NH or NR; and R, $R^2$, $R^3$, and $R^4$ are independently selected from the group consisting of ($C_1$–$C_{10}$) alkyl, ($C_3$–$C_{10}$) alkenyl, ($C_3$–$C_{10}$)alkynyl, ($C_3$–$C_{10}$) cycloalkyl, ($C_3$–$C_{10}$) cycloalkyl ($C_1$–$C_6$) alkyl, and ($C_1$–$C_4$) phenalkyl wherein these substituents may be substituted by one or more ($C_1$–$C_6$) alkyl, halo ($C_1$–$C_6$) alkyl, halogen, cyano, ($C_1$–$C_6$) alkoxy, halo ($C_1$–$C_6$) alkoxy, carbo ($C_1$–$C_6$) alkoxy or ($C_1$–$C_6$) acyl groups; and $R^3$ and $R^4$ may be joined to form a heterocyclic ring with up to seven atoms; and $X^4$ and $R^4$ may in combination be a pyrrolidine or piperidine ring; and with the proviso that only one of $R^2$, $R^3$ and $R^4$ may be a cycloalkyl group.

Typical compounds of the invention include, but are not limited to the examples shown in Table 1. Most preferred presently known compounds for control of the corn rootworm are compound numbers 11, 18, 19, 38, 41, 45, 46, 47, 57 and 65.

TABLE 1

$$\begin{array}{c} R^1 \\ \diagdown \\ O \\ \diagdown \\ P-NHNH-P \\ \diagup \\ X^2 \\ \diagup \\ R^2 \end{array} \begin{array}{c} S \\ \| \\ \end{array} \begin{array}{c} R^3 \\ \diagup \\ Y \quad X^3 \\ \| \diagup \\ \\ \diagdown \\ X^4 \\ \diagdown \\ R^4 \end{array} \quad (I)$$

| Cpnd. No. | $R_1$ | $R_2$ | $X_2$ | $R_3$ | $X_3$ | $R_4$ | $X_4$ | Y |
|---|---|---|---|---|---|---|---|---|
| 1 | Et | Et | O | Et | O | Et | O | S |
| 2 | Et | Et | O | Et | O | Et | O | O |
| 3 | Et | Et | O | | | —N—CH$_2$CH$_2$—N— | | S |
| | | | | | | \| \|    | | |
| | | | | | | CH$_3$     CH$_3$ | | |
| 4 | Et | Et | O | Et | O | Et | P—C bond | S |
| 5 | Et | Et | O | Et | O | i-Pr | O | S |
| 6 | Et | Et | O | Et | O | Pr | O | S |
| 7 | Et | Et | O | Et | O | Bu | O | S |
| 8 | Et | Et | O | Et | O | sec-Bu | O | S |
| 9 | Et | Et | O | i-Pr | O | i-Pr | O | S |
| 10 | Et | Et | O | Et | O | allyl | O | S |
| 11 | Et | Et | O | Et | O | i-Bu | O | S |
| 12 | Et | Et | O | Et | O | propargyl | O | S |
| 13 | Et | Et | O | Pr | O | Pr | O | S |
| 14 | Pr | Pr | O | Pr | O | Pr | O | S |
| 15 | Et | Et | O | Et | O | —CHMeCF$_3$ | O | S |
| 16 | Pr | Pr | O | i-Pr | O | i-Pr | O | S |
| 17 | Et | Bu | O | Pr | O | Pr | O | S |
| 18 | Pr | Pr | O | Et | O | i-Bu | O | S |
| 19 | Pr | Pr | O | Et | O | sec-Bu | O | S |
| 20 | Et | Et | O | Et | O | i-Pr | S | S |
| 21 | Et | Et | O | Et | O | Et | S | O |
| 22 | Pr | Pr | O | Et | O | Et | S | O |
| 23 | Pr | Pr | O | Et | O | i-Pr | S | S |
| 24 | Et | Et | O | Et | O | Pr | NH | S |
| 25 | Pr | Pr | O | Et | O | Pr | NH | S |
| 26 | Et | Et | O | Et | O | Et | S | S |
| 27 | Pr | Pr | O | Et | O | Et | O | S |
| 28 | Pr | Pr | O | Et | O | Pr | O | S |
| 29 | Et | Pr | O | Et | O | Pr | O | S |
| 30 | Me | Et | P—C bond | Me | O | Et | P—C bond | S |
| 31 | Et | Et | P—C bond | Et | O | Et | P—C bond | S |

TABLE 1-continued $$\begin{array}{c} R^1 \\ O \quad S \\ \diagdown \| \\ P-NHNH-P \\ \diagup \\ X^2 \\ R^2 \end{array} \begin{array}{c} R^3 \\ Y \quad X^3 \\ \| \diagup \\ \\ X^4 \\ R^4 \end{array} \quad (I)$$

| Cpnd. No. | R₁ | R₂ | X₂ | R₃ | X₃ | R₄ | X₄ | Y |
|---|---|---|---|---|---|---|---|---|
| 32 | Pr | Et | P—C bond | Pr | O | Et | P—C bond | S |
| 33 | Pr | Pr | O | Et | O | Et | P—C bond | S |
| 34 | Et | Et | O | Pr | O | O | OCH₂CMe₃ | S |
| 35 | Et | Et | O | Et | O | (+)menthyl | O | S |
| 36 | Et | Et | O | Me | O | Me | O | S |
| 37 | Pr | Pr | O | Me | O | Me | O | S |
| 38 | Et | Et | O | Et | O | —CH₂CMe₃ | O | S |
| 39 | Et | Et | O | Et | O | —CMe(CF₃)₂ | O | S |
| 40 | Et | Et | O | Et | O | —CMe₂CF₃ | O | S |
| 41 | Pr | Pr | O | Et | O | —CH₂CMe₃ | O | S |
| 42 | Me | Me | O | Me | O | Me | O | S |
| 43 | Me | Et | P—C bond | Et | O | Et | P—C bond | S |
| 44 | Me | Me | O | Et | O | —CH₂CMe₃ | O | S |
| 45 | Et | Pr | O | Et | O | —CH₂CMe₃ | O | S |
| 46 | Et | i-Pr | O | Et | O | —CH₂CMe₃ | O | S |
| 47 | Et | sec-Bu | O | Et | O | —CH₂CMe₃ | O | S |
| 48 | Et | —CMe(CF₃)₂ | O | Et | O | —CH₂CMe₃ | O | S |
| 49 | Et | Me | P—C bond | Et | O | —CH₂CMe₃ | O | S |
| 50 | Et | Et | P—C bond | Et | O | —CH₂CMe₃ | O | S |
| 31 | Me | Et | P—C bond | Et | O | —CH₂CMe₃ | O | S |
| 52 | Et | —CH₂CMe₃ | O | Et | O | sec-Bu | S | O |
| 53 | Et | Et | O | Et | O | sec-Bu | S | O |
| 54 | Et | Pr | O | Et | O | sec-Bu | S | O |
| 55 | Et | i-Pr | O | Et | O | sec-Bu | S | O |
| 56 | Et | sec-Bu | O | Et | O | sec-Bu | S | O |
| 57 | Et | —CH₂CMe₃ | O | —CH₂CMe₃ | O | —CH₂CMe₃ | O | S |
| 58 | Et | Me | P—C bond | Et | O | Me | P—C bond | S |
| 59 | Et | Et | O | —CH₂CMe₃ | O | —CH₂CMe₃ | O | S |
| 60 | Et | Et | O | Et | O | N-pyrrolidine | | S |
| 61 | Et | Et | O | | —O— | CH₂CMe₂CH₂ | —O— | S |
| 62 | Et | Et | O | Et | O | N-piperidine | | S |
| 63 | Et | Et | O | Et | O | amyl | O | S |
| 64 | Pr | Pr | O | Et | O | N-piperIdine | | S |
| 65 | Et | sec-Bu | O | Et | O | sec-Bu | O | S |
| 66 | Et | i-Bu | O | Et | O | i-Bu | O | S |
| 67 | Et | i-Pr | O | Et | O | i-Pr | O | S |
| 68 | Et | Et | O | i-Pr | O | —CH₂CMe₃ | O | S |
| 69 | Et | Pr | O | Et | O | —CMe₂CF₃ | O | S |
| 70 | Et | Pr | O | Et | O | —CMe(CF₃)₂ | O | S |
| 71 | Et | Et | O | Et | O | i-Bu | NH | S |
| 72 | Et | Et | O | Et | O | octyl | O | S |
| 73 | Et | Et | O | Et | O | Cyclohex(Me)₄ | O | S |
| 74 | Et | Et | O | Et | O | Bu | NH | S |
| 75 | Et | Et | O | Et | O | Et | NMe | S |
| 76 | Et | Et | O | Et | O | Pr | NMe | S |
| 77 | Et | Et | O | Et | O | hexyl | O | S |
| 78 | Et | Et | O | Et | O | —CH₂CF₂CF₃ | O | S |
| 79 | Pr | Pr | O | Et | O | amyl | O | S |
| 80 | Pr | Pr | O | Et | O | hexyl | O | S |
| 81 | Pr | Pr | O | Et | O | i-Bu | NH | S |
| 82 | Et | i-Pr | O | Pr | O | Pr | O | S |
| 83 | Et | i-Bu | O | i-Pr | O | i-Pr | O | S |

The term "halo" by itself or as a part of another substituent means chloro, fluoro, bromo and iodo.

The term "alkyl" by itself or as a part of another substituent, unless otherwise stated, means straight and branched chain groups such as methyl, ethyl, propyl, isopropyl, butyl, isobutyl, secbutyl, tertbutyl, pentyl, neopentyl, hexyl, heptyl, octyl, nonyl and decyl.

The term "haloalkyl" by itself or as a part of another substituent is an alkyl group of the stated number of carbon atoms having one or more halo atoms bonded thereto such as chloromethyl, bromoethyl, trifluoromethyl and bromodifluoromethyl.

The term "cycloalkyl" by itself or as a part of another substituent, unless otherwise stated, means carbocylic structures and alkyl substituted carbocycles such as cyclopropyl, cyclobutyl, cyclopentyl, cyclohexyl and menthyl.

The term "alkenyl" means straight and branched chain groups containing at least one carbon to carbon double bond such as propenyl, butenyl, pentenyl, hexenyl, heptenyl, octenyl, nonenyl and decenyl.

The term "alkynyl" means straight and branched chain groups containing at least one carbon to carbon triple bond such as propargyl, butynyl, pentynyl, hexynyl, heptynyl, octynyl, nonynyl and decynyl.

The term "heterocycle" or "heterocyclic ring" means a saturated or unsaturated ring containing up to seven atoms at least one of which is phosphorus.

The term "acyl" means a group having the structure: —C(=O)—R wherein R is an alkyl group having from one to six carbon atoms. The term "carboalkoxy" means a group having the structure —C(=O)—O—R wherein R is an alkyl group having from one to six carbon atoms.

The term "alkoxy" by itself or as a part of another substituent means a straight or branched alkyl group bonded to an oxygen atom and including straight and branched groups such as methoxy, ethoxy, isopropoxy, butoxy and neopentoxy.

The term "alkylthio" by itself or as a part of another substituent means a straight or branched alkyl group bonded to a sulfur atom and including such groups as methylthio, isopropylthio and secbutylthio.

The term "cycloalkoxy" by itself or as part of another substituent means carbocylic structures and carbocydic structures substituted by alkyl groups bonded to an oxygen atom and including such groups as cyclohexyloxy, cyclopentyloxy and menthyloxy.

The term "pesticidally or insecticidally effective amount" means a quantity of compound which causes a reduction of the pest or insect population or decreases crop damage compared to a control group.

As used in this disclosure, "corn rootworm" means the Western corn rootworm, *Diabrotica virgifera virgifera* and *Diabrotica virgifera* complex; the Northern corn rootworm, *Diabrotica barberi;* and the Southern corn rootworm, *Diabrotica undecimpunctata howardi.*

As used in this disclosure, the term "phosphoryl" means both phosphate and phosphonate compounds and their sulfur analogs.

In certain cases the compounds of this invention possess asymmetric centers which give rise to optical enantiomorphs and diastereomers. The compounds may also possess acidic or basic moieties which may form salts or metal complexes; this invention includes such enantiomorphs, salts and metal complexes.

The potential symmetry of the compounds of this invention may result in the equivalence of several possible representations of the same molecule.

The compositions and compounds of this invention can be applied directly to the locus to be protected, as for example, the area around or upon economic plants infected with insects or to plants on which infestation is to be prevented. The compounds and compositions may be used either as contact or systemic pesticides.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as "systemic" application. Alternatively, the active compound may be applied to the soil and contacted therein with the insects and other pests to be controlled. This means of application is referred to as "soil" application. In another alternative, the active compound may be foliarly applied to the plants to be freed from insects and other pests which feed on the foliage.

When using the compounds defined above, the method of invention is especially effective against soil insects when the active compound is applied on or in the soil in order to effect direct contact with the insects or other pests. By "pests" is meant organisms including arthropods, which in turn includes insects and acarids which organisms attack agricultural plants.

For use as pesticides, the compounds of this invention can be used a solutions, suspensions or mixtures in organic solvents or formulations. For example, they can be formulated as wettable powders, emulsifiable concentrates, dusts, granular formulations or flowable emulsifiable concentrates. In such formulations, the compounds of this invention are present at a concentration of about 0.00001 to about 99%, preferably about 1 to about 95%, and are extended with an agronomically acceptable liquid or solid carrier. When desired, suitable surfactants are likewise incorporated. Surfactants commonly used in the art can be found in the John W. McCutcheon, Inc. publication "Detergents and Emulsifiers Annual." Allured Publishing Co., Ridgewood, N.J.

By "agronomically acceptable carrier" is meant any substance which can be utilized to dissolve, disperse or diffuse the chemical incorporated therein without impairing the effectiveness of the toxic agent and which does not create permanent damage to such environment as soil, equipment, and agronomic crops when utilized according to recommendations.

The compounds of this invention can be taken up on or mixed with a finely particled solid carrier, as for example, clays, inorganic silicates, carbonates, and silicas. Organic carriers can also be employed.

Dust concentrates are commonly made wherein compounds are present in the range of about 20 to 80%. For ultimate applications, these concentrates are normally extended with additional solid to given an active ingredient content of from 0.1 to about 20%. Granular formulations are being made using a granular or pelletized form of carrier, such as granular days, vermiculite, charcoal or corn cobs, and may contain the active ingredient from about 1 to about 25% by weight.

Wettable powder formulations are made by incorporating the compounds of this invention in an inert, finely divided solid carrier along with a surfactant which can be one or more emulsifying, wetting, dispersing, or spreading agents or a blend of these. The compounds are usually present in the range of about 10 to about 80% by weight and surfactants in from about 0.5 to about 10% by weight. Commonly used emulsifying and wetting agents include polyoxyethylated derivatives of alkylphenols, fatty alcohols, fatty acids, alkylamines, alkylarene sulfonates and dialkyl sulfosuccinates. Spreading agents include such material as glycerol mannitan laureate and a condensate of polygylcerol and oleic acid modified with phthalic anhydride. Dispersing agents include such materials as the sodium salt of the copolymer of maleic anhydride and an olefin such as diisobutylene, sodium lignin sulfonate and sodium formaldehyde naphthalene sulfonates.

Water disposible granular products may be prepared by granulating or agglomerating a suitable wettable powder formulations which is compatable with the active ingredients. Agglomeration is carried out in a conventional manner such as by a pan agglomeratory. Dispersible granular products are described in U.S. Pat. No. 3,954,439 and British Pat. No. 1,433,882.

One convenient method for preparing a solid formulation is to impregnate the compounds of this invention onto the solid carrier by means of a volatile solvent, such as acetone. In this manner, adjuvants, such as activators, adhesives, plant nutrients, synergists and various surfactants can also be incorporated.

Emulsifiable concentrate formulations are prepared by dissolving the compounds of this invention in an agronomically acceptable organic solvent and adding a solvent-soluble emulsifying agent. Suitable solvents are usually waterimmiscible and can be found in the hydrocarbon, chlorinated hydrocarbon, ketone, ester, alcohol and amide classes of organic solvents. Mixtures of solvents are commonly employed. The surfactants useful as emulsifying agents can constitute about 0.5 to about 10% by weight of emulsifiable concentrates and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. In certain situations, however, it may be desirable and advantageous to apply the compounds directly onto the loci to be protected or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purpose of such application, the compound being utilized, the frequency of dissemination, and the like. For use as insecticides, dilute sprays can be applied at concentrations of about 0.01 to about 20 pounds of the active ingredients per 100 gallons of spray. They are usually applied at about 0.1 to about 5 pounds per 100 gallons. In more concentrated sprays, the active ingredient is increased by a factor of 2 to 40. With dilute sprays, applications are usually made to the plants until run-off is achieved, whereas with more concentrated or low-volume sprays, the materials are applied as mists. For use as a soil insecticide, the compounds can be applied as a dilute liquid preparation or as a solid formulation, preferably a granular formulation, by broadcasting, side-dressing, introduction into the seed furrow, soil incorporation, or seed treatment. The application rate can be from about 0.05 to about 10 pounds per acre of active ingredient and for economic reasons, preferably from about 0.1 to about 2 pounds per acre.

The compounds of this invention can be utilized as the sole pesticidal agents or they can be employed in conjunction with other bactericides, fungicides, herbicides, insecticides, acaricides, and comparable pesticides.

The compounds of this invention may be prepared by a variety of reaction schemes.

One method particularly useful for preparing the compounds is illustrated is the following reaction sequence.

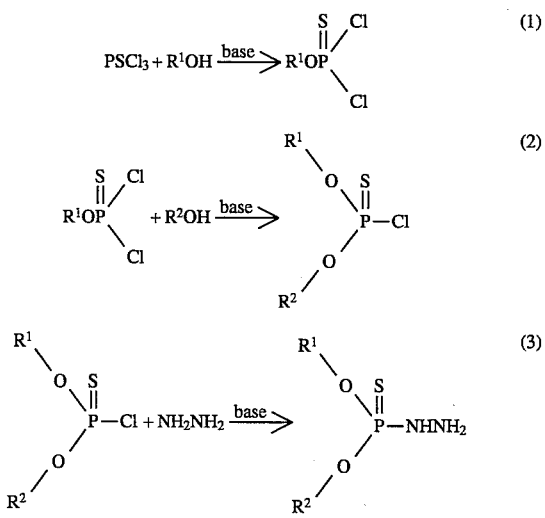

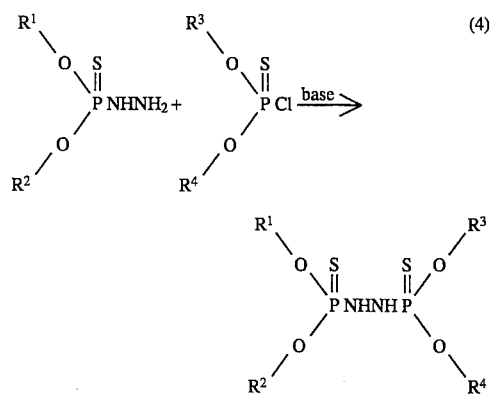

The above method is useful to react alcohols (as illustrated), mercaptans and amines with thiophosphoryl chloride to prepare the corresponding thiophosphoryl analog (Steps 1 and 2). Phosphorus oxychloride may be substituted for thiophosphoryl chloride to prepare the corresponding phosphoryl compounds.

Bases to neutralize the hydrogen halide produced in the reaction may be chosen from organic or inorganic materials such as potassium carbonate, sodium hydroxide, sodium hydride, pyridine, and the like.

Reaction temperature for the above reactions may be varied from about −50° C. to about 120° C., preferably from about −40° C. to about 60° C. The proper base, solvent, and reaction parameters for a particular reaction may be selected on the basis of the chemical and physical properties of the reagents. The above synthetic method may be adapted to prepare alkyl phosphorus compounds as follows:

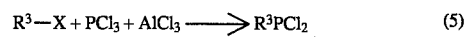

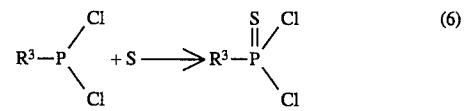

The dichlorothiophosphonyl intermediate produced by reaction (6) may be used as the starting material in reaction (2).

If desired, a second alkyl group may be introduced into the product of reaction (5).

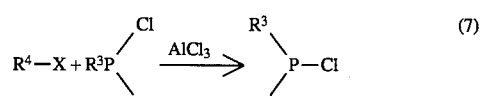

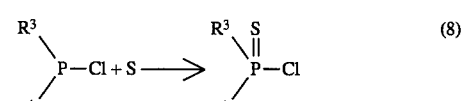

The product of reaction (8) may be used as the starting material for reaction (3).

The oxygen analogs of the intermediates and starting materials in reactions (1) through (8) may be substituted for the thiophosphoryl compounds illustrated in the reactions. Likewise, other halogens may be substituted for the chlorine shown in the reactions.

The required starting materials and intermediates to prepare the compounds of the invention are available from commercial sources or may be prepared by known reactions such as those illustrated above and described in Examples A to T given below. Other suitable reaction schemes will be obvious to the chemist of ordinary skill. Typical preparations are also described in U.S. Pat. Nos. 2,968,688 and 2,945,055 and *Synthesis of Carbon-Phosphorous Bonds* by Robert Engel, p. 172 CRC Press (1988).

The following examples are intended only to further illustrate the invention and are not intended to limit the scope of the invention which is defined by the claims.

PREPARATION OF INTERMEDIATES

Example A: Preparation of O,O,O-triethyl thiophosphate

To 402 g (1240 mmole) of a 21% solution of sodium ethoxide in ethanol was slowly added 72 g (425 mmole) of thiophosphoryl chloride. The resulting exotherm refluxed the mixture. After the addition was complete, the ethanol was removed in vacuo and the residue was partitioned between diethyl ether and water. The organic layer was dried over magnesium sulfate, concentrated in vacuo, and distilled (bp 100°–5° C. 20 torr) to yield 68 g of the title compound, an oil. nmr 1.4 t 9H, 4.3 m 6H.

Example B: Preparation of O,O-diethyl thiophosphate potassium salt

To 86 g (434 mmole) of O,O,O-triethyl thiophosphate in 300 ml of absolute ethanol was added 28 g (440 mmole) of 88% KOH. The resulting mixture was refluxed for 20 hours, filtered while warm, concentrated in vacuo, and triturated with 20% diethyl ether/80% hexanes to yield 67 g of the title compound, a white solid mp 192°–197° C.

Example C: Preparation of O,O-dipropyl thiophosphate potassium salt

To 100 g (460 mmole) of di-n-propylchlorothiophosphate in 300 ml of 1-propanol was added 58.8 g (920 mmole) of 88% potassium hydroxide pellets. The reaction mixture was refluxed overnight and then cooled to room temperature. The precipitated potassium chloride was filtered off and the solvent was stripped in vacuo. The resulting solid was slurried in 20% diethyl ether/80% hexanes and filtered yielding 67 g of the title compound, a fluffy white solid, mp 205°–207° C.

Example D: Preparation of O-ethyl O-propyl chlorothiophosphate

To 30 g (167 mmole) of O-ethyl dichlorothiophosphate in 100 ml of tetrahydrofuran (THF) and cooled to −70° C. was added a solution of sodium propoxide (from 7.4 g of 60% NaH (184 mmole) and 11 g (176 mmole) of 1-propanol) in 50 ml of THF. After warming to room temperature over 2 hours, the THF was removed in vacuo and the residue was partitioned between 50 ml diethyl ether, 50 ml hexanes, and 25 ml cold water. The organic layer was dried over magnesium sulfate, concentrated in vacuo, and distilled (bp 45°–50° C. 1 torr) yielding 20 g of the title compound, an oil. nmr 1.0 t 3H, 1.4 t 3H, 1.8 sextet 2H, 4.4M 4H.

Example E: Preparation of O,O-diisopropyl chlorothiophosphate

A solution of sodium isopropoxide in THF was prepared by the reaction of 45 g (1125 mmole) of 60% sodium hydride with 84 ml (1100 mmole) of isopropyl alcohol in 400 ml of THF. This solution was added, with mechanical stirring, to 83.4 g (490 mmole) of thiophosphorylchloride in 300 ml of THF and cooled to −40° C. internal. After the addition was complete the reaction mixture was slowly warmed to 25° C. When gas chromatography showed the reaction to be complete the THF was removed in vacuo and the product partitioned between hexanes and water. The organic layer was dried over anhydrous magnesium sulfate and concentrated in vacuo yielding 93 g of the title compound, an oil. nmr 1.4 d 12H, 4.9 m 2H.

Example F: Preparation of O-ethyl O-neopentyl chlorothiophosphate

By substantially following the procedure of Example D, using neopentyl alcohol in place of 1-propanol, one obtains the title compound, an oil. nmr 1.0 s 9H, 1.4 m 3H, 3.9 m 2H, 4.4 m 2H.

Example G: Preparation of O,O-dipropylthiophosphoryl hydrazine

To 70 ml (1400 mmole) of hydrazine monohydrate and 100 ml of methylene chloride cooled to −10° C. internal was slowly added with mechanical stirring 100 g (460 mmole) of O,O-dipropylchloro-thiophosphate. After stirring for 1 hour, the reaction mixture was diluted with hexanes and extracted with water. The organic layer was dried over anhydrous magnesium sulfate, filtered and concentrated in vacuo yielding the title compound, an oil. nmr 1.0 t 6H, 1.8 sextet 2H, 3.5 bdd 2H, 4.0 m 4H, 4.7 d 1H.

Example H: Preparation of O-ethyl O-isopropyl chlorothiophosphate

By substantially following the procedure of Example D, using isopropyl alcohol in place of 1-propanol, one obtains the title compound, an oil. nmr 1.4 m 9H, 4.3 m 2H, 5.0 m 1H.

Example I: Preparation of O-ethyl O-isopropylthiophosphoryl hydrazine

By substantially following the procedure of Example G, using O-ethyl O-isopropyl chlorothiophosphate one obtains the title compound, an oil. nmr 1.4 m 9H, 3.5 bs 2H, 4.1 dq 2H, 4.8 bd 1H, 4.8 m 1H.

Example J: Preparation of O-ethyl O-secbutyl chlorothiophosphate

By substantially following the procedure of Example D, using secbutyl alcohol in place of 1-propanol, one obtains the title compound, an oil. nmr 1.0 m 3H, 1.4 m 6H, 1.8 m 2H, 4.2 m 4H, 4.8 m 1H.

Example K: Preparation of O,O-diethylthiophosphoryl hydrazine

By substantially following the procedure of Example G, using O,O-diethyl chlorothiophosphate one obtains the title compound, an oil. nmr 1.4 t 6H, 3.5 bs 2H, 4.0 m 4H, 4.7 d 1H.

Example M: Preparation of O-ethyl O-isobutyl chlorothiophosphate

By substantially following the procedure of Example D, using isobutyl alcohol in place of 1-propanol, one obtains the title compound, an oil. nmr 1.0 m 6H, 1.4 m 3H, 2.1 m 1H, 4.0 m 2H, 4.3 m 2H.

Example N: Preparation of N-(O-ethyl O-neopentylthiophosphoryl)-N-methyl hydrazine By substantially following the procedure of Example G, using methyl hydrazine and O-ethyl O-neopentyl chlorothiophosphate (Example F) one obtains the title compound, an oil. nmr 1.0 s 9H, 1.4 t 3H, 2.9 d 3H, 3.7 m 4H, 4.2 m 2H.

Example O: Preparation of O-ethyl O-propylthiophosphoryl hydrazine

By substantially following the procedure of Example G, using O-ethyl O-propyl chlorothiophosphate (Example D) one obtains the title compound, an oil. nmr 1.0 t 3H, 1.4 t 3H, 1.8 sextet 2H, 3.5 bs 2H, 4.0 m 2H, 4.1 m 2H 4.7 d 1H.

Example P: Preparation of O-ethyl O-secbutylthiophosphoryl hydrazine

By substantially following the procedure of Example G, using O-ethyl O-secbutyl chlorothiophosphate (Example J)

one obtains the title compound, an oil. nmr 1.0 t 3H, 1.4 m 6H, 1.7 septet 1H, 3.4 bs 2H, 4.1 m 2H, 4.2 bd 1H, Example O: Preparation of O,O-dineopentyl chlorothiophosphate By substantially following the procedure of Example E using neopentyl alcohol instead of isopropyl alcohol one obtains the title compound, an oil. nmr 1.0 s 18H, 3.9 m 4H.

Example R: Preparation of O,O-dineopentylthiophosphoryl hydrazine

By substantially following the procedure of Example G, using O,O-dineopentyl chlorothiophosphate (Example Q) one obtains the title compound, an oil. nmr 1.0 s 18H, 3.4 bs 2H, 3.7 m 4H, 4.5 bd 1H.

Example S: Preparation of 0-ethyl 0-butyl chlorothiophosphate

By substantially following the procedure of Example D, using butyl alcohol in place of 1-propanol, one obtains the title compound, an oil. nmr 1.0 t 3H, 1.4 m 5H, 1.8 m 2H, 4.2 m 4H.

Example T: Preparation of O-ethyl O-neopentyl thiophosphate potassium salt

Sixty One grams (260 mmole) of O-ethyl O-neopentyl chlorothiophosphate and 33.7 g (530 mmole) of 88% potassium hydroxide were mixed in 300 ml of ethyl alcohol and stirred at 22° C. for 60 hours. The precipitated potassium chloride was filtered off and the ethyl alcohol removed in vacuo. The resulting solid was washed with hexanes and diethyl ether yielding the title compound, a white solid.

PREPARATION OF BISPHOSPHORYL HYDRAZINES

Example 11: N-(O,O-diethylthiophosphoryl) N'-(O-ethyl O-isobutylthiophosphoryl) hydrazine A mixture of 5.0 g (27 mmole) of O.O-diethylthiophosphoryl hydrazine (Example K), 6.5 g (29 mmole) O-ethyl O-isobutyl chlorothiophosphate (Example M), 50 ml. of THF and 4.0 g of potassium carbonate were refluxed for 24 hrs, concentrated in vacuo, and partitioned between diethyl ether and water. The organic layer was dried over anhydrous magnesium sulfate, concentrated in vacuo, and chromatographed on silica gel yielding 7.0 g of the title compound, an oil. nmr 1.0 m 6H, 1.4 m 9H, 2.0 septet 1H, 3.8 m 2H, 4.1 m 6H, 4.8 bd 2H.

Example 18: N-(O,O-dipropylthiophosphoryl) N'-(O-ethyl O-isobutylthiophosphoryl) hydrazine By substantially following the procedure given for Compound 11 6.0 g (28 mmole) of O,O-dipropylthiophosphoryl hydrazine (Example G) and 6.7 g (31 mmole) of O-ethyl O-isobutyl chlorothiophosphate (Example M) were reacted to yield 7.0 g of the title compound, an oil. nmr 1.0 m 12H, 1.4 t 3H, 1.7 m 4H, 2.0 septet 1H, 3.8 m 2H, 4.0 m 4H, 4.1 m 2H, 4.9 bd 2H.

Example 19: N-(O,O-dipropylthiophosphoryl) N'-(O-ethyl O-secbutylthiophosphoryl) hydrazine By substantially following the procedure given for Compound 11 6.0 g (28 mmole) of O,O-dipropylthiophosphoryl hydrazine (Example G) and 6.7 g (31 mmole) of O-ethyl O-secbutyl chlorothiophosphate (Example J) were reacted to yield 7.0 g of the title compound, an oil. nmr 1.0 m 9H, 1.4 m 6H, 1.7 m 6H, 4.0 m 6H, 4.6 m 1H, 4.7 dd 2H.

Example 38: N-(O,O-diethylthiophosphoryl) N'-(O-ethyl O-neopentylthiophosphoryl) hydrazine Five grams (24 mmole) of O,O-diethylthiophosphoryl hydrazine (Example K) and 1.1 g (36 mmole) of 80% sodium hydride were reacted in 20 ml of THF, then 6.0 g (24 mmole) of O-ethyl O-neopentyl chlorothiophosphate (Example F) was added and the mixture was stirred at 25° C. for 1 hour. Workup with diethyl ether and water followed by silica gel chromatography yielded 6.2 g of the title compound, an oil. nmr 1.0 m 9H, 1.4 m 6H, 3.7 m 2H, 4.1 m 6H, 4.9 bdd 2H.

Example 41: N-(O,O-dipropylthiophosphoryl) N'-(O-ethyl O-neopentylthiophosphoryl) hydrazine By substantially following the procedure given for Compound 38 6.0 g (25 mmole) of O,O-dipropylthiophosphoryl hydrazine (Example G) and 6.2 g (25 mmole) of O-ethyl O-neopentyl chlorothiophosphate (Example F) yielded 7.8 g of the title compound, an oil. nmr 1.0 m 15H, 1.4 t 3H, 1.8 sextet 4H, 3.7 m 2H, 4.1 m 6H, 4.8 bdd 2H.

Example 45: N-(O-ethyl O-propylthiophosphoryl) N'-(O-ethyl O-neopentylthiophosphoryl) hydrazine By substantially following the procedure given for Compound 38 3.3 g (16 mmole) of O-ethyl O-propylthiophosphoryl hydrazine (Example 0) and 4.0 g (16 mmole) of O-ethyl O-neopentyl chlorothiophosphate (Example F) yielded 5.8 g of the title compound, an oil. nmr 1.0 m 12H, 1.4 t 6H, 1.7 m 2H, 3.7 m 2H, 4.0 m 2H, 4.1 m 2H, 4.8bdd 2H.

Example 46: N-(O-ethyl O-isopropylthiophosphoryl) N'-(O-ethyl O-neopentylthiophosphoryl) hydrazine To 11.0 g (55 mmole) of O-ethyl O-isopropylthiophosphoryl hydrazine (Example I) and 12.5 g (54 mmole) of O-ethyl O-neopentyl chlorothiophosphate (Example F) in 6 g (76 mmole) of pyridine was warmed in at 60° C. for 1 hour and cooled. The reaction mixture was partitioned between ether and dilute aqueous hydrochloric acid. The organic layer was dried, concentrated, and chromatographed on silica gel using 5% ethyl acetate in hexanes yielding 12.7 g of the title compound an oil. nmr 0.9 s 9H, 1.4 m 12H, 3.8 m 2H, 4.2 m 4H, 4.8 bd 2H, 4.9 m 1H Example 47: N-(O-ethyl O-secbutylthiophosphoryl) N'-(O-ethyl O-neopentylthiophosphoryl) hydrazine By substantially following the procedure given for Compound 38 3.7 g (16 mmole) of O-ethyl O-secbutylthiophosphoryl hydrazine (Example P) and 4.0 g (16 mmole) of O-ethyl O-neopentyl chlorothiophosphate (Example F) yielded 5.8 g of the title compound, an oil. nmr 1.0 m 12H, 1.4 m 9H, 1.7 m 2H, 3.7 m 2H 4.1 m 4H, 4.7 m 3H.

Example 57: N-(O,O-dineopentylthiophosphoryl) N'-(O-ethyl O-neopentylthiophosphoryl) hydrazine By substantially following the procedure given for Compound 38 6.0 g (22 mmole) of O,O-dineopentylthiophosphoryl hydrazine (Example R) and 5.6 g (22 mmole) of O-ethyl O-neopentyl chlorothiophosphate (Example F) yielded 10.0 g of the title compound, an oil. nmr 1.0 s 27H, 1.4 t 3H, 3.8 m 6H, 4.2 m 2H, 4.8 bd 2H.

Example 65: N-(O-ethyl O-secbutylthiophosphoryl) N'-(O-ethyl O-secbutylthiophosphoryl) hydrazine By substantially following the procedure given for Compound 38 5.1 g (23 mmole) of O-ethyl O-secbutylthiophosphoryl hydrazine (Example P) and 5.0 g (23 mmole) of O-ethyl O-secbutyl chlorothiophosphate (Example J) yielded 7.0 g of the title compound, an oil. nmr 1.0 t 6H, 1.4 m 12H, 1.7 m 4H, 4.1 m 4H, 4.6 m 2H, 4.7 bd 2H.

BIOLOGICAL METHODS

Biological Method A: Corn Rootworm Screening Test

A parent solution containing 600 parts per million (ppm) of the test compound was made by dissolving the test compound in a solvent (acetone: methanol,1:1) and adding water to give an acetone:methanol:water system of 5:5:90 and then a surfactant was utilized at the equivalent of 1 ounce per 100 gal. of test solution. The surfactant consisted of a 1:1 mixture of an alkylarylpolyetheralcohol (Rohm and Haas Co. Triton® X-155) and a modified phthalic glycerol alkyl resin (Rohm and Haas Co. Triton® B-1956).

Test solutions were made by serially diluting the 600 ppm parent solution with water and surfactant to give concentrations of 150, 38, 10, 2.5, and 0.6 ppm.

Ten ml of each test solution were pipetted into 190 gm of a non-sterile loamy soil (pH 5.5 to 7.0) contained in a 16 oz glass jar. This application provided soil concentrations of 8, 2, 0.5, 0.125, and 0.03 ppm. Each jar was shaken to insure uniform distribution of chemical in the soil. Soil moisture ranged from 18% to 22%.

In this soil, organophosphate and carbamate soil insecticides (e.g., Dyfonate® and Furadan®), used as test standards, effectively controlled the corn rootworm. This soil was considered a "non-aggressive soil".

The southern corn rootworm, *Diabrotica undecimpunctata howardi*, was used as the test insect.

Two presoaked corn (*Zea mays* var. Golden Cross Bantam) seeds were placed in the bottom of a 1 oz. plastic cup and covered with about 30 gm. of treated soil. The soil surface of each cup was inoculated with southern corn rootworm eggs resulting in a larval challenge of 50 to 70 larvae per cup. The cups were closed with tight fitting snap caps.

The test cups were held for 10 days at 27° C. and then the percent kill relative to the infested check was determined. Mortalities obtained were plotted on logarithmic probability paper (No. 3228, Codex Book Co. Inc., Norwood, Mass.). The estimated concentration eliciting a 90% mortality (LC90) was established from the best eye-fitted line to the plotted mortality data.

Biological Method B: Corn Rootworm Foliar Systemic Application Test

A parent solution containing 600 parts per million (ppm) of the test compound was made by dissolving the test compound in a solvent (acetone: methanol,1:1) and adding water to give an acetone:methanol:water system of 5:5:90 and then a surfactant was utilized at the equivalent of 1 ounce per 100 gal. of test solution. The surfactant consisted of a 1:1 mixture of an alkylarylpolyetheralcohol (Rohm and Haas Co. Triton ® X-155) and a modified phthalic glycerol alkyl resin (Rohm and Haas Co. Triton ® B-1956).

Test solutions were made by serially diluting the 600 ppm parent solution with water and surfactant to give concentrations of 120 and 60 ppm.

The southern corn rootworm, *Diabrotica undecimpunctata howardi*, was used as the test insect.

Corn (*Zea mays*, var. Golden Cross Bantam) plants in the 6-leaf stage, growing in individual 8 inch plastic pots in the greenhouse, were infested with southern corn rootworm eggs. Rootworm eggs, suspended in a 0.125% agar solution, were pipetted into the soil to a depth of approximately 4 cm providing an infestation of approximately 400 eggs per plant.

The test soil was non-sterile Iowa topsoil with a natural population of microorganisms that cause enhanced microbial degradation of certain organophosphate and carbamate soil insecticides (e.g. Dyfonate® and Furadan®) used as test standards. This "aggressive soil" rendered these chemicals ineffective when applied to the soil for controlling the corn rootworm.

Three days post-infestation with corn rootworm eggs, the soil surface of each pot was masked with an absorbent material and the plant sprayed to runoff with the test solution using a DeVilbiss atomizer at 20 psig. Four plants were sprayed at each concentration. When dry, each treatment was maintained under greenhouse conditions. Plants were watered as needed.

Fourteen days post-spraying with the test compound the plants were uprooted, the roots thoroughly rinsed with water to remove the soil, and rated for corn rootworm larval feeding damage using the following modified Iowa Corn Root Rating System:

Damage Rating Description of Root System

1 No noticeable feeding damage

2 Feeding scars present but no root pruning

3 At least one root pruned but less than an entire node of roots pruned

4 At least one full node of roots pruned but less than two full nodes

5 Two or more full nodes pruned

Each root system in the group of four treated plants was scored individually and a group average was calculated. A treatment provided acceptable corn rootworm control with an average root damage rating of 1.0 to 3.0 and unacceptable control with an average root damage rating of >3.0 to 5.0.

The average root system damage ratings were converted to percent control relative to the infested check.

Biological Method C: Corn Rootworm At Planting Soil Application Test

A test solution containing technical compound to provide a row application rate (40 inch distance between rows) to soil of 0.5 lb ai/acre was made by dissolving 46 mg of test compound in 20 ml of solvent (acetone:methanol,1:1), adding 580 ml of water, and then a surfactant at the equivalent of 1 ounce per 100 gal of test solution. The surfactant consisted of a 1:1 mixture of an alkylarylpolyetheralcohol (Rohm and Haas Co. Triton® X-155) and a modified phthalic glycerol alkyl resin (Rohm and Haas Co. Triton® B-1956).

Solutions for lower application rates of 0.25, 0.125, and 0.0625 lb ai/acre were made in the same manner using proportionately less technical compound.

Two corn (*Zea mays* var Golden Cross Bantam) seeds were planted approximately one inch deep in the center of the soil contained in an 8 inch plastic pot. Immediately after planting, 150 ml of the test solution was poured evenly over the soil surface in each pot. Four pots were treated at each application rate. Each treatment was maintained under greenhouse conditions. Pots were watered as needed. Upon seed germination, plant stand was reduced to one plant per pot.

The southern corn rootworm, *Diabrotica undecimpunctata howardi*, was used as the test insect.

The test soil was non-sterile Iowa topsoil with a natural population of microorganisms that cause enhanced microbial degradation of certain organophosphate and carbamate soil insecticides (e.g. Dyfonate® and Furadan®) used as test standards. This "aggressive soil" rendered these chemicals ineffective when applied to the soil for controlling the corn rootworm.

Four weeks post-planting, each pot was infested with southern corn rootworm eggs. Rootworm eggs, suspended in a 0.125% agar solution, were pipetted into the soil to a depth of approximately 4 cm providing an infestation of approximately 400 eggs per plant.

Seventeen days post-infestation with corn rootworm eggs, the plants were uprooted, the roots thoroughly rinsed with water to remove the soil, and rated for corn rootworm larval feeding damage using the following modified Iowa Corn Root Rating System:

Damage Rating Description of Root System

1 No noticeable feeding damage

2 Feeding scars present but no root pruning

3 At least one root pruned but less than an entire node of roots pruned

4 At least one full node of roots pruned but less than two full nodes

5 Two or more full nodes pruned

Each root system in the group of four treated plants was scored individually and a group average was calculated. A treatment provided acceptable corn rootworm control with an average root damage rating of 1.0 to 3.0 and unacceptable control with an average root damage rating of >3.0 to 5.0.

The average root system damage ratings were converted to percent control relative to the infested check. Mortalities obtained were plotted on logarithmic probability paper (No. 3228, Codex Book Co. Inc., Norwood, Mass.). The estimated concentration eliciting a 90% mortality (LC90) was established from the best eye-fitted line to the plotted mortality data.

Table 2 sets forth the melting points and biological data obtained by methods A and C on corn rootworm as described above for the exemplary compounds of Table 1.

Biological Method D: Foliar Insecticidal Activity Test

In evaluating the foliar insecticidal activity of the compounds of this invention against insects and mites, the following test procedures were employed.

A test solution containing 600 parts per million (ppm) was made by dissolving the test compound in a solvent (acetone:methanol, 1:1), adding a surfactant and then water to give an acetone:methanol:water system of 5:5:90. A 1:1 mixture of an alkylarylpolyetheralcohol (Triton® X-155 surfactant from Rohm and Haas Company, Philadelphia, Pa.) and a modified phthalic glycerol alkyl resin (Triton® B-1956 surfactant from Rohm and Haas Company, Philadelphia, Pa.) was utilized at the equivalent of 1 ounce per 100 gal. of test solution as a surfactant.

Analogous solutions were made by serially diluting the 600 ppm test solution with water and surfactant to give concentrations of 150, 38, 10, 2.5, 0.6, 0.15 and 0.038 ppm. Not all compounds were tested at each of the several concentrations stated above. Test concentrations of a compound were selected as those most likely to differentiate dose response of a particular compound toward a particular test insect.

Initial evaluations were made on one or more of the following pests:

| Code Symbol | Common Name | Latin Name |
|---|---|---|
| AW | Southern Armyworm | *Spodoptera eridania* |
| BB | Mexican Bean Beetle | *Epilachna varivestis* |
| GPA | Green Peach Aphid | *Myzus persicae* |
| TSM | Two-Spotted Spider Mite | *Tetranychus urticae* |
| BW | Boll Weevil | *Anthonomus grandis* |

For the Mexican Bean Beetle and Southern armyworm tests, individual lima bean (*Phaseolus limeniss* var. Woods' Prolific) leaves were placed on moistened pieces of filter paper in Petri dishes. The leaves were then sprayed with the test solution using a rotating turntable and allowed to dry. The dishes were then infested with 10 third instar larvae of either the Mexican Been Beetle or the Southern Armyworm. The dishes were then covered. Percent mortality was determined for each species and spray concentration at 48 and 96 hours after treatment.

For the mite test, infested bean (*Phaseolus limensis* var. Woods Prolific) leaf discs (1.25" in diameter) containing about 50 mites were placed in a Petri dish lid on a moistened piece of cotton. The leaves were then sprayed to thorough wetness with the test solution using a rotating turntable, held for twenty-four hours and then the percentage killed was determined.

For the aphid test, infested broccoli (*Brassica oleracea italica* var. DiCicco) leaves containing about 50 aphids were placed in a Petri dish lid on a moistened piece of cotton. The leaves were then sprayed to thorough wetness with the test solution using a rotating turntable, held for twenty-four hours and then the percentage killed was determined.

For the boll weevil test, 10 adult weevils were placed in a 0.5 pint glass Mason jar containing a small cube of apple. The weevils were confined to the jar by fiberglass screen mesh secured by a screw-type rim cap. The jars were then sprayed with the test solution using a rotating turntable; directing the spray through the mesh into the jar. The percentage killed was determined after forty-eight and ninety six hours.

The mortalities obtained in this manner were plotted on logarithmic probability paper. The estimated concentration eliciting a 50 percent mortality (LC50) was established from the best eye-fitted line to the plotted mortality data.

The rotating turntable consists of a fixed, continuously operating spray nozzle under which targets are rotated at a fixed speed and distance. If the target is a Petri dish (such as for the bean beetle, armyworm, mite, or aphid tests), the distance from the nozzle is 15 inches. If the target is a Mason jar (such as for the boll weevil test), the distance from the nozzle is 7 inches. The nozzle is located 8 inches from the rotating shaft. The targets on individual platforms revolve around the shaft at 1 revolution per 20 seconds but only a brief portion of this time occurs in the spray path. Targets pass only once under the nozzle and then are removed to drying hoods.

The nozzle used is a ¼ JCO Spraying Systems (Wheaton, Ill.) air atomizing nozzle equipped with a No. 2850 fluid cap and a No. 70 air cap. At the 10 psig air pressure used and with liquid siphon feed, 0.5 GPH (gallons per hour) are delivered in a round spray pattern with a 21 degree spray angle. Targets are misted with spray droplets to the point that the droplets coalesce to form a uniform thin film insufficient to drown test organisms.

Results of foliar evaluation are set forth in Table 3.

Biological Method E: Turf Grub Insecticidal Activity Test

A test solution containing 150 parts per million (ppm) was made by dissolving the test compound in a solvent (acetone:methanol, 1:1), adding a surfactant and then water to give an acetone:methanol:water system of 5:5:90. A 1:1 mixture of an alkylarylpolyetheralcohol (Rohm and Haas Co. Triton® X-155 ) and a modified phthalic glycerol alkyl resin (Rohm and Haas Co. Triton® B-1956) was utilized at the equivalent of 1 ounce per 100 gal. of test solution as a surfactant.

Analogous solutions were made by serially diluting the 160 ppm test solution with water and surfactant to give concentrations of 40, 20, 10, and 5 ppm active ingredient. These will give soil concentrations of 1.6, 0.8, 0.4, and 0.2 pounds per acre, respectively.

Ten milliliters of test solution were incorporated into 250 ml of moistened soil (clay loam, 90%: humus soil, 10%) and allowed to air in an uncapped pint jar for about 2 hours. After airing, a small amount of seed mixture containing equal parts of redtop (*Agrostis alba*) and white clover (*Trifolium repens*) was incorporated into the soil. Two 50 ml quantities of soil were placed into dep 3 ounce ointment tin cans.

Ten Japanese beetle (*Popillia japonica*) eggs were placed into the soil in each can and the can capped with its tined lid. Treatments were held for 23 days at 30 degrees Centigrade.

Upon termination, the soil was sieved to isloate the grubs. The percent mortality was determined for each concentration. Mortalities obtained were plotted on logarithmic probability paper (No. 3228, Codex Book Co. Inc., Norwood, Mass.). The estimated concentration eliciting a 95 percent mortality (LC95) was established from the best eye-fitted line to the plotted mortality data.

Results of Turf Grub Test are set forth in Table 4.

TABLE 2

Corn Rootworm Activity of Bisphosphoryl Hydrazines

| Comp. no. | primary nonagressive Method A crw LC90 ppm | foliar systemic nonagressive Method B crw % control at 0.5 lb./acre | secondary aggressive Method C crw LC50 lb./acre | MP |
|---|---|---|---|---|
| 1 | 0.5 | 16 | I | 73 |
| 2 | 0.87 | 0 | I | 80 |
| 3 | 4.5 | NT | I | 126 |
| 4 | 0.84 | 64 | −1.7 | 75–77 |
| 5 | <0.1 | 69 | I | 49–50 |
| 6 | <0.1 | 23 | I | 55–56 |
| 7 | 0.25 | 38 | I | oil |
| 8 | <0.1 | 53 | 0.72 | oil |
| 9 | 0.41 | 64 | 0.98 | oil |
| 10 | 0.79 | 34 | I | 46–47 |
| 11 | <0.1 | 53 | 0.32 | oil |
| 12 | 0.56 | 30 | I | 42 |
| 13 | <0.1 | 46 | I | 45 |
| 14 | 0.39 | 46 | 1.0 | 66 |
| 15 | <0.1 | 54 | I | oil |
| 16 | 0.95 | 46 | 0.92 | oil |
| 17 | 1.1 | 38 | 0.91 | oil |
| 18 | <0.1 | 61 | 0.32 | oil |
| 19 | <0.1 | 54 | 0.25 | oil |
| 20 | 0.40 | 50 | 0.90 | oil |
| 21 | 4.7 | NT | NT | oil |
| 22 | I | NT | NT | oil |
| 23 | 0.55 | 16 | I | oil |
| 24 | 1.1 | 38 | I | oil |
| 25 | 2.5 | NT | NT | oil |
| 26 | 1.1 | NT | I | 59–60 |
| 27 | 5.8 | NT | I | semi-sol |
| 28 | 1.1 | NT | 0.95 | 52 |
| 29 | 0.09 | 38 | −2.7 | 47 |
| 30 | I | NT | NT | 154–155 |
| 31 | 1.2 | NT | I | 116–117 |
| 32 | 2.7 | NT | I | 127–128 |
| 33 | 3.1 | NT | I | 43 |
| 34 | 1.1 | NT | 0.58 | oil |
| 35 | 0.77 | 38 | NT | oil |
| 36 | 0.90 | NT | I | oil |
| 37 | 1.7 | NT | NT | oil |
| 38 | 0.07 | 46 | 0.45 | oil |
| 39 | 0.71 | 46 | I | oil |
| 40 | 1.0 | NT | I | oil |
| 41 | 0.06 | 31 | 0.27 | oil |
| 42 | I | NT | I | 66 |
| 43 | 5.3 | NT | I | 126-127 |
| 44 | 0.37 | NT | 0.50 | oil |
| 45 | 0.39 | NT | 0.33 | oil |
| 46 | 0.08 | NT | 0.30 | oil |
| 47 | 0.09 | NT | 0.34 | oil |
| 48 | 0.40 | NT | 0.56 | oil |
| 49 | 1.1 | NT | 0.84 | oil |
| 50 | 1.1 | NT | I | oil |
| 51 | 1.1 | NT | 0.5–1.0 | oil |
| 52 | 1.1 | NT | 0.70 | oil |
| 53 | 1.6 | NT | NT | oil |

TABLE 2-continued

Corn Rootworm Activity of Bisphosphoryl Hydrazines

| Comp. no. | primary nonagressive Method A crw LC90 ppm | foliar systemic nonagressive Method B crw % control at 0.5 lb./acre | secondary aggressive Method C crw LC50 lb./acre | MP |
|---|---|---|---|---|
| 54 | 1.1 | NT | I | oil |
| 55 | 1.1 | NT | I | oil |
| 56 | 1.1 | NT | I | oil |
| 57 | 1.1 | NT | 0.45 | oil |
| 58 | I | NT | NT | 134–135 |
| 59 | I | NT | I | 55 |
| 60 | 1.1 | NT | I | 74 |
| 61 | 1.1 | NT | I | 104 |
| 62 | 1.1 | NT | I | 65 |
| 63 | 1.1 | NT | I | oil |
| 64 | 8.6 | NT | I | 52 |
| 65 | 0.09 | NT | 0.39 | oil |
| 66 | 0.09 | NT | −1.7 | oil |
| 67 | 0.09 | NT | I | oil |
| 68 | 1.1 | NT | I | oil |
| 69 | 1.1 | NT | I | oil |
| 70 | 1.1 | NT | I | oil |
| 71 | 1.1 | NT | I | oil |
| 72 | 1.1 | NT | I | oil |
| 73 | 1.1 | NT | 0.67 | 90–91 |
| 74 | 1.1 | NT | 0.92 | oil |
| 75 | 1.1 | NT | I | oil |
| 76 | 1.1 | NT | I | oil |
| 77 | 1.1 | NT | I | oil |
| 78 | 1.1 | NT | I | oil |
| 79 | 1.1 | NT | I | oil |
| 80 | 1.1 | NT | I | oil |
| 81 | 1.1 | NT | I | oil |
| 82 | 0.7 | NT | 0.85 | oil |

NT = Not Tested
I = Inactive at Rate Tested

TABLE 3

Insecticidal and Miticidal Activity of Bisphosphoryl Hydrazines Method D/LC50 in ppm

| Cpd. | TSM | GPA | BB 48 hrs. | BB 96 hrs | AW 48 hrs | AW 96 hrs | BW 48 hrs | BW 96 hrs |
|---|---|---|---|---|---|---|---|---|
| 1 | I | 500 | I | I | I | 500 | I | I |
| 2 | 540 | 150 | I | I | I | I | I | I |
| 3 | I | I | I | I | I | I | I | I |
| 4 | I | I | I | I | I | I | 740 | I |
| 5 | 150 | I | 740 | I | I | I | I | I |
| 6 | 150 | I | 420 | I | I | I | I | I |
| 7 | 150 | I | I | I | I | I | I | I |
| 8 | 335 | I | 500 | 84 | I | I | I | 740 |
| 9 | 76 | I | 300 | 150 | I | I | I | I |
| 10 | 510 | I | I | 78 | I | I | I | I |
| 11 | I | I | 150 | 60 | I | I | I | 740 |
| 12 | I | I | 150 | 62 | I | I | I | I |
| 13 | I | I | 150 | 52 | I | I | I | I |
| 14 | I | I | 500 | 52 | I | I | I | I |
| 15 | I | I | 150 | 62 | I | I | I | I |
| 16 | I | I | 150 | 62 | I | I | I | I |
| 17 | I | I | 150 | 62 | I | I | I | I |
| 18 | I | I | 150 | 78 | I | I | I | I |
| 19 | I | I | 78 | 62 | I | I | I | I |
| 20 | I | I | 110 | 52 | I | I | I | I |
| 21 | I | I | I | I | I | I | I | I |
| 22 | I | I | 150 | 115 | I | I | I | I |
| 23 | 150 | 150 | 62 | 78 | I | I | I | I |
| 24 | I | I | 27 | 31 | I | I | I | 380 |
| 25 | I | 1 | 38 | 13 | I | I | I | I |
| 26 | 640 | I | 150 | 150 | I | I | I | I |
| 27 | I | I | 150 | 150 | I | I | I | 740 |

TABLE 3-continued

Insecticidal and Miticidal Activity of Bisphosphoryl Hydrazines
Method D/LC50 in ppm

| Cpd. | TSM | GPA | BB 48 hrs. | BB 96 hrs | AW 48 hrs | AW 96 hrs | BW 48 hrs | BW 96 hrs |
|---|---|---|---|---|---|---|---|---|
| 28 | I | I | 62 | 50 | I | I | I | I |
| 29 | 150 | I | 150 | 150 | 420 | 180 | I | I |
| 30 | I | I | I | I | I | I | I | I |
| 31 | I | I | I | I | I | I | I | I |
| 32 | I | I | I | I | I | I | I | 740 |
| 33 | I | I | 500 | 45 | I | I | I | I |
| 34 | I | I | I | 52 | I | I | I | I |
| 35 | I | I | 250 | 52 | I | I | I | I |
| 36 | 79 | I | I | 600 | I | I | I | I |
| 37 | 450 | I | 150 | 62 | I | I | I | I |
| 38 | 150 | I | 60 | 60 | I | I | 740 | 740 |
| 39 | 150 | I | 31 | 150 | I | I | I | I |
| 40 | 150 | I | 38 | 45 | I | I | I | I |
| 41 | I | I | 62 | 78 | I | I | I | I |
| 42 | 150 | I | 600 | I | I | I | I | I |
| 43 | 1 | I | I | I | I | I | I | 600 |
| 44 | I | I | I | I | I | 500 | 380 | 380 |
| 45 | I | I | I | I | I | 150 | I | 150 |
| 46 | I | I | I | 45 | I | I | I | I |
| 47 | I | I | I | 45 | I | I | I | I |
| 48 | I | I | I | I | 300 | 150 | I | I |
| 49 | I | I | 115 | 70 | I | I | I | I |
| 50 | I | I | I | 150 | I | I | I | I |
| 51 | I | I | 740 | 200 | I | I | I | I |
| 52 | I | I | 500 | 150 | I | I | I | I |
| 53 | I | I | I | I | I | I | 740 | 740 |
| 54 | I | I | I | I | 52 | I | I | 11 |
| 55 | I | I | I | 17 | I | I | 740 | 70 |
| 56 | I | I | 380 | 31 | I | I | I | I |
| 57 | I | 1 | I | I | I | I | I | I |
| 58 | I | I | I | I | I | I | I | I |
| 59 | I | I | I | I | I | I | 740 | 740 |
| 60 | I | I | I | I | I | I | I | I |
| 61 | I | I | I | I | I | I | 740 | 740 |
| 62 | I | I | I | I | I | I | I | I |
| 63 | I | I | I | 740 | I | I | 1 | 740 |
| 64 | I | I | 740 | 740 | I | I | I | I |
| 65 | 245 | I | 360 | 62 | I | I | I | I |
| 66 | I | I | I | 150 | I | I | I | I |
| 67 | 150 | I | 150 | 62 | I | I | I | I |
| 68 | 520 | I | 500 | 150 | I | I | I | I |
| 69 | 360 | I | 500 | 62 | I | I | I | I |
| 70 | I | I | 500 | 45 | I | I | I | I |
| 71 | I | I | 150 | 150 | I | I | I | I |
| 72 | I | I | I | I | I | I | I | I |
| 73 | I | I | I | 740 | I | I | I | I |
| 74 | I | I | 740 | 380 | I | I | I | I |
| 75 | 150 | I | 500 | 150 | I | I | I | I |
| 76 | 150 | I | 150 | 62 | I | I | I | I |
| 77 | I | I | 150 | 150 | I | I | I | I |
| 78 | 150 | I | 360 | 150 | I | I | I | I |
| 79 | I | I | 380 | 62 | I | I | I | I |
| 80 | I | I | I | I | I | I | I | I |
| 81 | I | I | 500 | 740 | I | I | I | I |
| 82 | I | I | 500 | 150 | I | — | — | — |
| 83 | I | I | 500 | 62 | I | — | — | — |

I = inactive at concentration listed
— = not listed

TABLE 4

Turf Grub Insecticidal Activity Test
Method E/LC95 in pounds per acre

| Cpd. | LC95 | |
|---|---|---|
| 41 | <0.2 | |
| 46 | <0.2 | |
| Dursban | <0.2 | a commercial standard |

Although the invention has been described with regard to its preferred embodiments, which constitute the best mode presently known to the inventors, it should be understood that various changes and modifications as would be obvious to one having ordinary skill in this art may be made without departing from the scope of the invention, which is set forth in the claims.

We claim:

1. A soil application insecticidal compound of the formula:

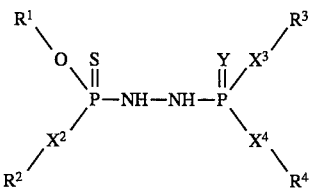

wherein $R^1$ is selected from the group consisting of $(C_1-C_4)$ alkyl which has no branching on the carbon adjacent to the oxygen, $(C_3-C_8)$ alkenyl or $(C_3-C_8)$ alkynyl wherein these substituents may be substituted with one or more halogen, cyano, $(C_1-C_6)$ alkoxy, halo $(C_1-C_6)$ alkoxy, carbo $(C_1-C_6)$ alkoxy, or $(C_1-C_6)$ acyl groups;

Y is oxygen or sulfur; and $X^2$, $X^3$ and $X^4$ are independently NH or NR; and R, $R^2$, $R^3$, and $R^4$ are independently selected from the group consisting of $(C_1-C_{10})$ alkyl, $(C_3-C_{10})$ alkenyl, $(C_3-C_{10})$ alkynyl, $(C_3-C_{10})$ cycloalkyl, $(C_3-C_{10})$ cycloalkyl $(C_1-C_6)$ alkyl, and $(C_1-C_4)$ phenalkyl wherein those substituents may be substituted with one or more $(C_1-C_6)$ alkyl, $(C_1-C_6)$ haloalkyl, halogen, cyano, $(C_1-C_6)$ alkoxy, halo $(C_1-C_6)$ alkoxy, carbo $(C_1-C_6)$ alkoxy, or $(C_1-C_6)$ acyl groups; and with the proviso that only one of $R^2$, $R^3$ and $R^4$ may be a cycloalkyl group.

2. A method of controlling corn rootworm, comprising applying to said corn rootworm soil habitat a pesticidally-effective amount of a compound of the formula

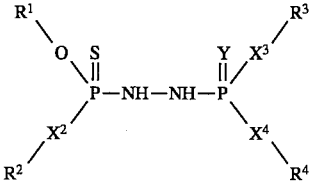

wherein $R^1$ is selected from the group consisting of $(C_1-C_4)$ alkyl which has no branching on the carbon adjacent to the oxygen atom, $(C_3-C_8)$ alkenyl or $(C_3-C_8)$ alkynyl wherein these substituents may be substituted with one or more halogen, cyano, $(C_1-C_6)$ alkoxy, halo $(C_1-C_6)$ alkoxy, carbo $(C_1-C_6)$ alkoxy, or $(C_1-C_6)$ acyl groups;

Y is oxygen or sulfur; and $X^2$, $X^3$ and $X^4$ are independently NH or NR; and R, $R^2$, $R^3$, and $R^4$ are independently selected from the group consisting of $(C_1-C_{10})$ alkyl, $(C_3-C_{10})$ alkenyl, $(C_3-C_{10})$ alkynyl, $(C_3-C_{10})$ cycloalkyl, $(C_3-C_{10})$ cycloalkyl $(C_1-C_6)$ alkyl, and $(C_1-C_4)$ phenalkyl wherein these substituents may be substituted by one or more $(C_1-C_6)$ alkyl, halo $(C_1-C_6)$ alkyl, halogen, cyano, $(C_1-C_6)$ alkoxy, halo $(C_1-C_6)$ alkoxy, carbo $(C_1-C_6)$ alkoxy or $(C_1-C_6)$ acyl groups; and with the proviso that only one of $R^2$, $R^3$ and $R^4$ may be cycloalkyl.

3. A method of controlling soil insects, comprising applying to said insect habitat a pesticidally-effective amount of a compound of the formula

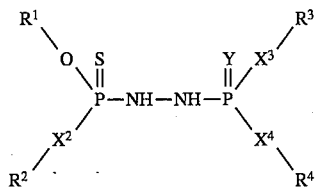

wherein $R^1$ is selected from the group consisting of ($C_1$–$C_4$) alkyl which has no branching on the carbon adjacent to the oxygen, ($C_3$–$C_8$) alkenyl or ($C_3$–$C_8$) alkynyl wherein these substituents may be substituted with one or more halogen, cyano, ($C_1$–$C_6$) alkoxy, halo ($C_1$–$C_6$) alkoxy, carbo ($C_1$–$C_6$) alkoxy, or ($C_1$–$C_6$) acyl groups;

Y is oxygen or sulfur; and $X^2$, $X^3$ and $X^4$ are independently NH or NR; and R, $R^2$, $R^3$, and $R^4$ are independently selected from the group consisting of ($C_1$–$C_{10}$) alkyl, ($C_3$–$C_{10}$) alkenyl, ($C_3$–$C_{10}$) alkynyl, ($C_3$–$C_{10}$) cycloalkyl, ($C_3$–$C_{10}$) cycloalkyl ($C_1$–$C_6$) alkyl, and ($C_1$–$C_4$) phenalkyl wherein those substituents may be substituted with one or more ($C_1$–$C_6$) alkyl, ($C_1$–$C_6$) haloalkyl, halogen, cyano, ($C_1$–$C_6$) alkoxy, halo ($C_1$–$C_6$) alkoxy, carbo ($C_1$–$C_6$) alkoxy, or ($C_1$–$C_6$) acyl groups; and with the proviso that only one of $R^2$, $R^3$ and $R^4$ may be a cycloalkyl group.

* * * * *